United States Patent [19]
McLaughlin

[11] Patent Number: 6,086,564
[45] Date of Patent: Jul. 11, 2000

[54] WRIST-MOUNTED I. V. ADMINISTRATION SET

[76] Inventor: David L. McLaughlin, 1502 W. Main St., Greenwood, Mo. 64034

[21] Appl. No.: 09/122,941

[22] Filed: Jul. 27, 1998

[51] Int. Cl.[7] ...................................................... A61M 5/32
[52] U.S. Cl. .................. 604/179; 604/180; 128/DIG. 26; 128/DIG. 6
[58] Field of Search ..................................... 604/174, 177, 604/179, 180; 128/DIG. 6, DIG. 26

[56] References Cited

U.S. PATENT DOCUMENTS

| | | | |
|---|---|---|---|
| 4,605,397 | 8/1986 | Ligon et al. ............................. | 604/179 |
| 4,769,010 | 9/1988 | Fenton, Jr. et al. ..................... | 604/180 |
| 5,037,398 | 8/1991 | Buchanan ................................ | 604/180 |
| 5,234,410 | 8/1993 | Graham et al. . | |
| 5,368,801 | 11/1994 | Vaillancourt . | |
| 5,472,430 | 12/1995 | Vaillancourt et al. . | |
| 5,509,912 | 4/1996 | Vaillancourt et al. . | |
| 5,514,116 | 5/1996 | Vaillancourt et al. . | |
| 5,690,617 | 11/1997 | Wright .................................... | 604/179 |
| 5,788,215 | 8/1998 | Ryan ................................... | 251/149.6 |
| 5,797,869 | 8/1998 | Martin et al. ............................. | 604/43 |

*Primary Examiner*—Corrine McDermott
*Attorney, Agent, or Firm*—Hovey, Williams, Timmons & Collins

[57] ABSTRACT

A patient infusion assembly (10) is provided having a synthetic resin infusion body (12) supported on a flexible adhesive mount (14) allowing the assembly (10) to be secured on a patient's body at a desired infusion site. The body (12) includes a plurality of elongated, tubular, substantially rigid infusion elements (16–20) each having an input end (40–44) and connected to a common outlet head (32). The elements (16–20) have individual fluid-conveying lumens (34–38) which communicate with corresponding outlet head passageways (62–66) in order to maintain the separation of respective infusion fluids prior to administration thereof. The outlet head (32) is equipped with a luer connector (60) allowing the ready attachment of a conventional infusion needle (67). Preferably, the elements (16–20) diverge from the connection head (32) with the longitudinal axis of the central element (18) disposed above the axes of the other elements (16, 20). One element (18) has a one-way duckbill-type check valve (54) in the lumen thereof.

11 Claims, 2 Drawing Sheets

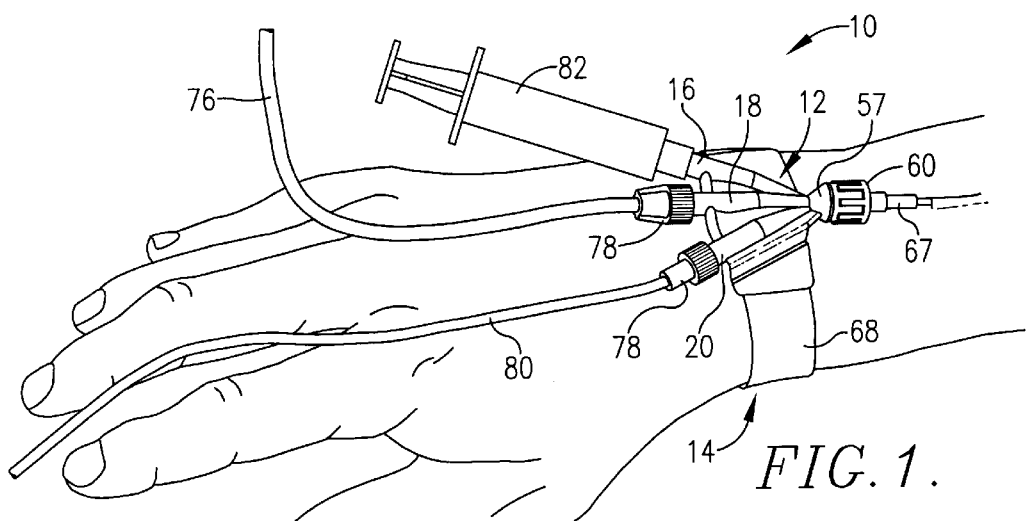
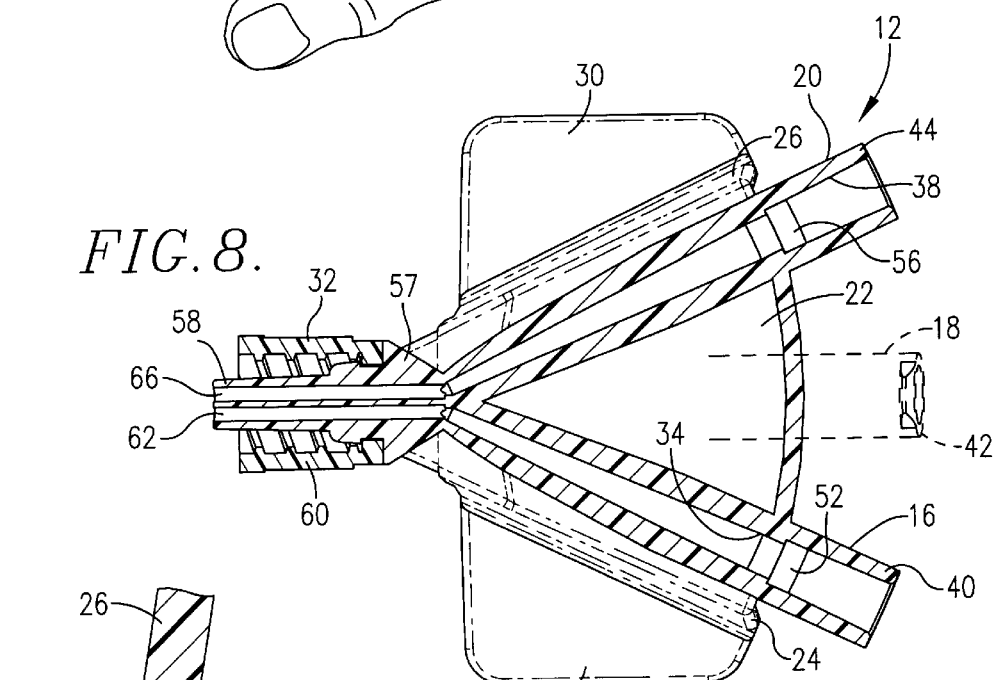
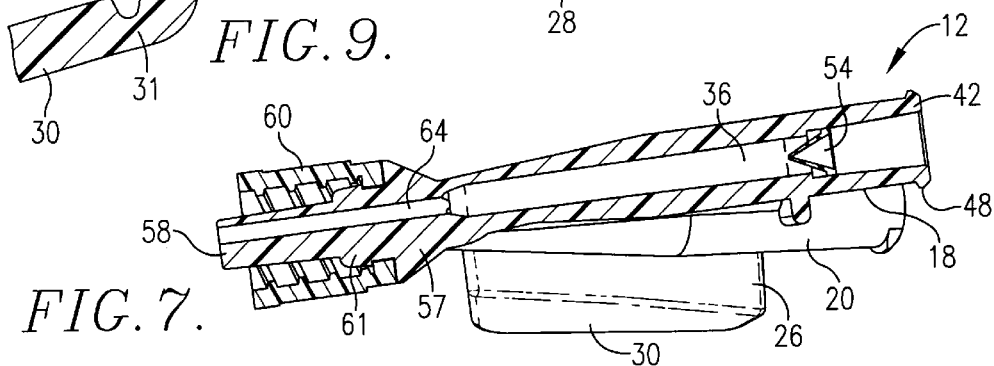

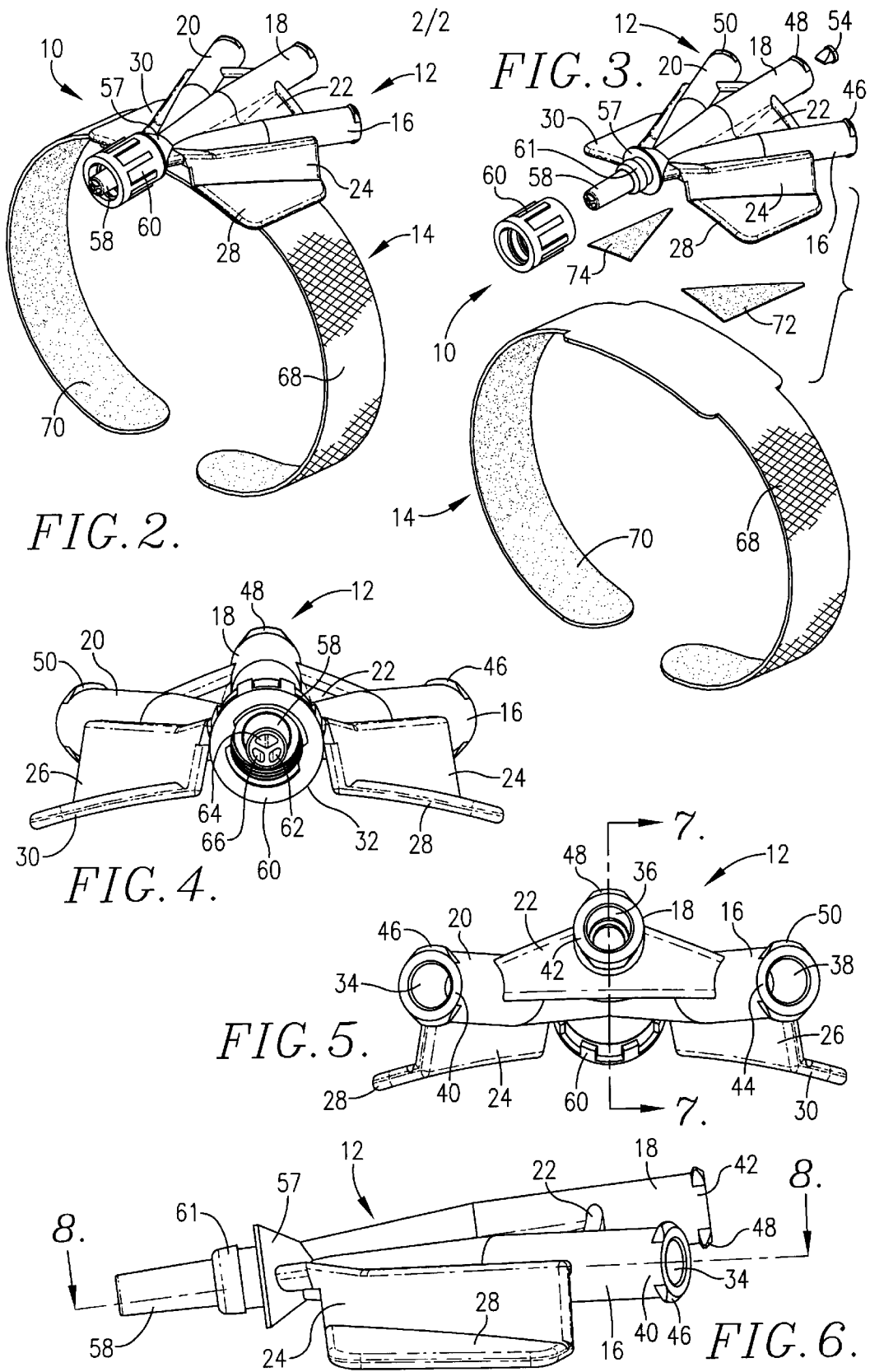

WRIST-MOUNTED I. V. ADMINISTRATION SET

BACKGROUND OF THE INVENTION

1. Field of the Invention

The present invention is broadly concerned with an improved patient infusion assembly permitting the safe infusion of multiple fluids into a patient, while eliminating the possibility of premixing of the fluids and minimizing the incidence of tangling of infusion lines. More particularly, the invention pertains to such an infusion assembly preferably made up of an injection molded, substantially rigid infusion body having a plurality of individual, tubular elements operably connected to a common outlet head; each of the elements has an input end for connection to a source of liquid whereas the outlet head is equipped with connection structure in order to couple the head with an infusion needle on the like. The infusion body is connected to a mount permitting securement of the assembly on a patient's body.

2. Description of the Prior Art

Many hospital patients, particularly those suffering from acute illnesses or in intensive care units, require infusion of multiple fluids on a continuous and/or periodic basis. For example, a patient may need continuous infusion of glucose solution to replenish body fluids, as well as medicaments either continuously or from time-to-time. It is important in such treatments that the individual fluids be properly infused without premixing thereof. Specifically, some types of medicaments can be rendered harmful or even fatal if they are mixed with other medicaments prior to infusion.

The traditional approach for infusing multiple fluids has involved insertion of an infusion needle into the patient at a desired location, along with a cannula which is connected with a flexible drip line. The needle is removed and the cannula is then commonly secured by tape to the patient's body. If additional fluids need infusion, it has been known to insert a secondary needle into the primary infusion line, through use of a Y connector, so that the second fluid can be administered through the primary line. In order to avoid the premixing problem, it is common to clamp the primary line upstream of the secondary needle during the infusion of the additional fluid(s). However, this procedure tends to create a partial vacuum in the primary line, called retrograde feedback. When the clamp is removed, portions of the secondary fluids may combine with the primary fluid. Thus, the fluids may be inadvertently premixed as a consequence of the procedure used to avoid premixing.

Attempts have been made to avoid problems inherent in the traditional infusion procedures by providing a common head connected to an infusion needle and having multiple short flexible inputs. Such prior devices have been constructed by hospital personnel on an as-need improvised basis, but are deficient in that they do not entirely avoid the premixing problem. Moreover, these devices provide fluid inputs which are closely adjacent each other and flexible, thus exacerbating the line tangling problem.

There is accordingly a need in the art for an improved infusion assembly which maintains the separation of individual fluids to be infused, eliminates the possibility of vacuum-induced reverse flow of fluids and separates the fluid inlets so that the fluid input lines can be safely maintained in a separated condition.

SUMMARY OF THE INVENTION

The present invention overcomes the problems outlined above and provides a patient infusion assembly broadly including an infusion body for multiple fluid inputs, together with a mount supporting the body and having structure permitting detachable mounting thereof on a patient's body, typically around the wrist.

In preferred forms, the infusion body is of integral synthetic resin construction and presents a plurality of individual, substantially rigid tubular elements each operably connected with a single common outlet head. Each of the elements has an input end adapted for connection to a source of liquid to be infused, and a lumen for conveying such liquid to the outlet head. The outlet head has a plurality of delivery passageways therethrough respectively in communication with a corresponding lumen, as well as connection structure permitting coupling with an infusion unit, normally a conventional infusion needle.

The infusion body preferably has three tubular elements arrayed so that the longitudinal axes thereof are oriented at an acute angle relative to each other. Moreover, the longitudinal axes of at least one of the elements is spaced above the longitudinal axes of the other elements. A flexible, duckbill-type check valve is located in the center, or gravity feed lumen of the tubular elements, which permit infusion of fluid but prevents vacuum-induced reverse flow of fluid from that element. Another feature of the invention is the ability of the care provider to withdraw a blood sample from the patient through either the left or right element of the body.

The preferred mount is a flexible, adhesive-coated strap which can be conveniently applied to a desired body site. The infusion body is in turn adhesively secured to the strap mount.

BRIEF DESCRIPTION OF THE DRAWINGS

FIG. 1 is an elevational view depicting the patient infusion assembly of the invention mounted on a patient's wrist, with a pair of flexible infusion lines coupled to respective tubular elements of the infusion body, and with a syringe coupled to the remaining tubular elements.

FIG. 2 is a perspective view of the infusion assembly depicted in FIG. 1, as it would appear before use thereof;

FIG. 3 is an exploded perspective view illustrating the components and construction of the infusion assembly of FIG. 2;

FIG. 4 is a front elevational view of the infusion body forming a part of the overall infusion assembly, and depicting the connection structure of the outlet head of the body;

FIG. 5 is a rear elevational view of the infusion body, illustrating the input ends of the individual tubular elements of the body;

FIG. 6 is a side elevational view of the infusion body;

FIG. 7 is a vertical sectional view taken along line 7—7 of FIG. 5;

FIG. 8 is a sectional view taken along line 8—8 of FIG. 6; and

FIG. 9 is a greatly enlarged, fragmentary sectional view illustrating the connection hinge regions between the support wings and the remainder of the infusion body.

DETAILED DESCRIPTION OF THE PREFERRED EMBODIMENT

Turning now to the drawings, and particularly FIGS. 2–3, a patient infusion assembly 10 in accordance with the invention broadly includes a molded, synthetic resin, multiple-port infusion body 12 detachably supported on a mount 14 allowing the assembly to be operatively secured to a desired portion of a patient's body such as the arm and particularly the wrist. The assembly 10 is designed to safely and conveniently permit attachment of multiple infusion lines and/or syringes as illustrated in FIG. 1.

In more detail, the infusion body 12 (FIGS. 4–9) is of integral design and includes a total of three essentially identical tubular elements 16, 18, 20 with an interconnecting support web 22 therebetween, a pair of side segments 24, 26 depending from web 22, and outermost wing sections 28, 30. As best seen in FIG. 9, each of the wing sections is flexible to a slight degree relative to the remainder of body 12, by provision of a formed, relatively thin hinge region 31 between each wing and the adjacent side segment. In addition, the body 12 has a central common outlet head 32 extending forwardly from web 22.

Each of the tubular elements 16–20 is in the form of an elongated member presenting an internal, converging lumen 34, 36, 38 with an input end 40, 42, 44 having external connection ribs 46, 48, 50. The longitudinal axes of the elements 16–20 are each oriented at an acute angle relative to each other and converge to join head 32 as best seen in FIG. 8. In addition, as illustrated in FIG. 5, the central element 18 is oriented with the axis thereof somewhat above the axes of the side elements 16 and 20. The central element 18 is equipped with an internal, flexible duckbill-type check valve 54.

The outlet head 32 includes a conical abutment 57 as well as an elongated central section 58 and a tubular luer connector 60 detachably coupled to section 58 and engaging abutment 57; as best seen in FIG. 8, section 58 has a radially enlarged shoulder 61 spaced from abutment 57 permitting snap-fit rotatable connection of the luer connector 60. The section 58 has three elongated internal passageways 62, 64, 66 respectively in communication with the lumens 34, 36, 38 of the elements 16, 18, 20. The ends of the passageways 62–66 remote from the elements 16–20 are illustrated in FIG. 4. The elongated central section 58 and luer connector 60 allow attachment of an infusion unit such as a standard luer-type infusion needle 67 to the head 32 (FIG. 1).

The mount 14 in the embodiment shown is in the form of a flexible synthetic resin strap 68 which is designed to wrap at least partially around a patient's extremity, most commonly the wrist. The inner surface of strap 68 has pressure sensitive skin adhesive 70 thereon, allowing the strap to be releasably detached to the patient's body. As best seen in FIG. 3, the body 12 is attached to strap 68 by means of double faced adhesive patches 72, 74 which are affixed to the underside of the wing sections 28, 30. Thus, the elements 16–20 and web 22 are located in spaced relationship from the strap 68.

In the use of assembly 10, the strap 68 supporting infusion body 12 is secured on the patient's wrist or other desired site by adhering the strap 68 to the site; preferably, the adhesive 70 is hypoallergenic to eliminate the possibility of skin irritation. Next, the infusion needle 67 is inserted through the patient's skin adjacent the attachment site and is connected to head 32 by means of luer connector 60. At this point the input ends of the elements 16–20 are connected to appropriate sources of liquid to be infused. As an example (FIG. 1), it will be seen that the central element 18 is connected to an infusion line 76 coupled to a drip bag or the like. The line 76 is secured to the element 18 by a conventional connector device 78 which engages the element ribs 48. Similarly, a line 80 connected to an infusion pump is attached to one of the other elements 16 or 20, again using a connector 78. The remaining element can be used for periodic infusion of liquid medicaments by a conventional syringe 82 or for convenient withdrawal of a blood sample, negating the necessity of repeatedly resticking for blood samples. In this case the free element is typically capped until needed, whereupon the cap is removed and the outlet end of the syringe is inserted into the lumen of the element, and the plunger of the syringe used to inject the liquid medicament.

As will be clear from a study of FIGS. 7 and 8, the flow paths for the individual fluids to be administered are entirely separate from each other throughout infusion body 12. Thus, each element lumen is communication with a corresponding head passageway so as to eliminate the possibility of mixing the fluids prior to infusion thereof. Also, the duckbill valve 54 associated with the element 18 prevents any possibility of retrograde feedback backup, through the gravity feed line extender drip between the element 18 and the fluid supply container connected to that line.

In prior IV devices, when the supply line from the gravity feed container is clamped off, as often is the case, this clamping force can create a vacuum condition within the line above the Y connector and below the clamp, possibly retrograde feedback from other sources or from valve injection. This unintended mixing of medicament can cause significant patient trauma. This unintended mixing of incompatable medicine is to be avoided, which is accomplished with the present invention.

It will also be appreciated that provision of the substantially rigid elements 16–20 in a diverging, nonaligned array facilitates the separation of the individual fluid inputs, and minimizes the possibility of line tangling.

I claim:

1. A multi-lumen, intravenous administration assembly for mounting on a patient's arm adjacent a catheter inserted into the patient's vein, comprising:

an integral, relatively rigid infusion body of synthetic resin material and having a plurality of individual tubular elements operably connected with a single outlet head having an outlet end, each of said elements having an input end adapted for connection with a source of liquid to be infused into the patient's vein, and a liquid-conveying lumen extending through each tubular element from a corresponding input end to said outlet head, said outlet head having a plurality of liquid delivery passageways extending therethrough, there being one passageway for each of said tubular elements with each passageway being in direct communication only with a corresponding lumen and opening outwardly through said outlet end of the outlet head;

connection structure associated with said outlet head for releasably coupling the outlet end of the head to a catheter inserted in the patient's arm vein; and a mount constructed to support said infusion body on the patient's arm with at least the tubular elements being disposed in angular disposition relative to the mount such that the input ends thereof are spaced sufficiently above the adjacent surface of the patient's arm to permit ready connection of said input ends of respective tubular elements to sources of liquid, said mount including structure permitting detachable mounting of the infusion body on the patient's arm.

2. The assembly of claim 1, said body having three of said tubular elements.

3. The assembly of claim 2, the longitudinal axis of at least one of said tubular elements being spaced above the longitudinal axes of another of said tubular elements.

4. The assembly of claim 1, the longitudinal axes of said tubular elements being oriented at an acute angle relative to each other.

5. The assembly of claim 1, one of said tubular elements including a check valve located in the lumen thereof.

6. The assembly of claim 1, said elements being located in spaced relationship to said mount.

7. The assembly of claim 1, said infusion body having a pair of side marginal wing sections each engaging said mount, and respective upright segments extending upwardly from said wing sections, said elements supported by said upright segments.

8. The assembly of claim 1, said connection structure comprising a luer connector adapted to receive and couple an infusion needle.

9. The assembly of claim 1, said infusion body being detachably secured to said mount.

10. The assembly of claim 1, each of said element input ends including connection ribs for securement of an infusion line thereto.

11. A multi-lumen, intravenous administration assembly for mounting on a patient's arm adjacent a catheter inserted into a patient's vein, comprising:

an infusion body presenting a plurality of individual, substantially rigid tubular elements operably connected with a single outlet head, each of said elements having an input end adapted for connection with a source of liquid to be infused and a lumen for conveying said liquid to said outlet head, said outlet head having a plurality of delivery passageways each of which is in communication with a corresponding lumen of the tubular elements;

connection structure associated with said outlet head for releasably coupling the outlet end of the head to a catheter inserted in the patient's arm vein; and a mount supporting said infusion body and having structure permitting detachable mounting of the infusion body on the patient's body, said mount including a flexible strap having adhesive on one face thereof permitting the mount to be adhered to the patient's body.

* * * * *